United States Patent
Vazzana et al.

(10) Patent No.: US 11,248,992 B2
(45) Date of Patent: Feb. 15, 2022

(54) SYSTEMS AND METHODS FOR ACCESSING AND MONITORING A FLUID WITHIN A PRESSURIZED PIPE

(71) Applicant: Hydra-Stop LLC, Burr Ridge, IL (US)

(72) Inventors: Christopher C. Vazzana, Palos Park, IL (US); Andrew J. Nelson, Chicago, IL (US)

(73) Assignee: Hydra-Stop LLC, Burr Ridge, IL (US)

( * ) Notice: Subject to any disclaimer, the term of this patent is extended or adjusted under 35 U.S.C. 154(b) by 86 days.

(21) Appl. No.: 16/576,344

(22) Filed: Sep. 19, 2019

(65) Prior Publication Data

US 2020/0096422 A1   Mar. 26, 2020

Related U.S. Application Data

(60) Provisional application No. 62/733,900, filed on Sep. 20, 2018.

(51) Int. Cl.
| | |
|---|---|
| *G01N 1/20* | (2006.01) |
| *F16L 41/04* | (2006.01) |
| *F16L 55/07* | (2006.01) |
| *G01N 33/18* | (2006.01) |

(52) U.S. Cl.
CPC ............ *G01N 1/2035* (2013.01); *F16L 41/04* (2013.01); *F16L 55/07* (2013.01); *G01N 33/18* (2013.01); *G01N 2001/205* (2013.01)

(58) Field of Classification Search
CPC ........ F16L 55/07; F16L 41/04; G01N 1/2035; G01N 33/18
USPC .................................. 137/317, 318
See application file for complete search history.

(56) References Cited

U.S. PATENT DOCUMENTS

| | | |
|---|---|---|
| 1,045,289 A | 11/1912 | Dole |
| 4,485,668 A | 12/1984 | Hudson et al. |
| 4,651,558 A | 3/1987 | Martin et al. |
| 4,682,624 A | 7/1987 | Turner |
| 4,949,744 A * | 8/1990 | Heed et al. ............... F16K 7/10 |
| | | 137/15.15 |
| 5,121,644 A | 6/1992 | Grey et al. |
| (Continued) | | |

FOREIGN PATENT DOCUMENTS

DE      202012002473 U1      5/2012

OTHER PUBLICATIONS

GB Search Report for related Application No. 1913546.6; dated Jul. 14, 2020.

*Primary Examiner* — Kevin L Lee
(74) *Attorney, Agent, or Firm* — von Briesen & Roper, s.c.

(57) ABSTRACT

Systems and methods for accessing and monitoring a fluid within a pressurized pipe include a nozzle coupled to a section of the pressurized pipe and defining an open proximal end fluidly communicating with the pressurized pipe through an access hole formed in the pressurized pipe, an open distal end, and an interior passage extending from the open proximal end to the open distal end. A cover plate is coupled to the open distal end of the nozzle. A valve element is disposed in the interior passage and movable between an open position, in which the valve element is entirely disposed within the nozzle, and a closed position, in which a proximal section of the valve element is disposed in the pressurized pipe. A sensor port extends through a proximal end of the nozzle and positioned to fluidly communicate with the interior passage when the valve element is in the open position.

20 Claims, 5 Drawing Sheets

(56) References Cited

U.S. PATENT DOCUMENTS

| | | | |
|---|---|---|---|
| 5,186,199 A | 2/1993 | Murphy et al. | |
| 5,660,199 A | 8/1997 | Maichel | |
| 6,341,619 B1* | 1/2002 | Beninga | E03B 7/072 |
| | | | 137/318 |
| 6,640,827 B1 | 11/2003 | McClure | |
| 6,810,903 B1 | 11/2004 | Murphy et al. | |
| 6,889,703 B2 | 5/2005 | Bond | |
| 7,331,215 B2 | 2/2008 | Bond | |
| 7,357,605 B2 | 4/2008 | Weiler | |
| 8,627,843 B2 | 1/2014 | Ries | |
| 9,485,715 B2 | 11/2016 | Ansari | |
| 9,644,779 B2 | 5/2017 | Vazzana et al. | |
| 9,933,329 B2 | 4/2018 | Hansen et al. | |
| 2008/0309072 A1 | 12/2008 | Dole | |
| 2015/0247602 A1 | 9/2015 | Vazzana et al. | |
| 2016/0252072 A1* | 9/2016 | Peleg | F16L 41/04 |
| | | | 137/15.08 |
| 2019/0011071 A1* | 1/2019 | Gorintin et al. | F17D 3/18 |

\* cited by examiner

SYSTEMS AND METHODS FOR ACCESSING AND MONITORING A FLUID WITHIN A PRESSURIZED PIPE

FIELD

The present disclosure generally relates to maintenance and monitoring of pressurized pipes, and more particularly to systems and methods for accessing and monitoring a fluid within a pressurized pipe.

BACKGROUND

Pressurized conduits or pipes convey fluids, both liquid and gas, in municipalities, industrial plants, and commercial installations. When originally installed, a network of pipes typically includes strategically located isolation valves or block valves, which are used to isolate certain downstream sections of the pipe for repairs, relocation, and installation of new components into the pipe. When repair or maintenance of a pipe used in a municipal water system is required, however, inoperable isolation valves may need to be replaced, and the locations of existing isolation valves may necessitate the installation of additional isolation valves.

A hot tapping procedure may be used during pipe repair or maintenance to minimize service disruption. In a hot tapping procedure, a new access point into the pipe is formed while the fluid inside the pipe remains at an operable pressure. For example, commonly assigned U.S. Pat. Nos. 8,627,843 and 9,644,779 disclose methods of installing additional gate valves in pressurized pipes that do not require service interruption and result in minimal fluid or pressure loss. The additional gate valves connect to the pipe as an assembly using a permanent housing known as a valve housing that is sealably clamped to the pipe and normally extends upward. A temporary gate valve is sealably mounted on the open top of the valve housing (i.e., the distal end of the valve housing). One or more "tap" or installation housings and a tapping machine are mounted on top (distal end) of the temporary gate valve for delivering a cutting device through the temporary gate valve to the proximal end of the valve housing to cut a hole or "coupon" in the exposed pipe. After removal of the cutting device and closure of the temporary gate valve, the same or similar installation housings are mounted on the distal end of the temporary gate valve for delivering the gate valve cartridge through the temporary gate valve and to the interior of the valve housing, where it is housed while in the open position. This procedure is accomplished without depressurizing the pipe.

Instead of adding a gate valve to a pipe that may remain as a permanent fixture as disclosed in the '843 and '779 patents, sometimes all that is desired is to stop the flow through the pipe just upstream of a repair or maintenance location without installing a gate valve. In this case, a line stop is used to temporarily isolate the pipe at or upstream of the site of the repair or maintenance, while keeping the remainder of the system in operation. Similar to the '843 and '779 patents, commonly assigned U.S. Pat. No. 6,810,903 discloses a system that includes the use of a line stop fitting mounted to the pipe and a temporary gate valve mounted on top of the line stop fitting. Using appropriate housings and a tapping machine mounted on top of the temporary gate valve, a cutting device is inserted through the temporary gate valve to cut an opening in the pipe. After removal of the cutting device and closure of the temporary gate valve, a pump and ram with a housing are used to insert a line stop through the temporary gate valve and line stop fitting and into the pipe temporarily (see FIGS. 1-16 of the '903 patent) to stop the flow through the pipe. After a temporary line stop is withdrawn through the temporary gate valve, a completion plug is inserted through the temporary gate valve and into the line stop fitting to seal the line stop fitting so the temporary gate valve may be removed (see FIG. 16 of the '903 patent).

Separately or simultaneous with such repair and maintenance procedures, pipe diagnostics, condition assessment, and on-going monitoring may be performed. Current hot-tapping methods and systems do not facilitate sensing and monitoring of fluid conditions in a pressurized pipe.

SUMMARY

In accordance with one aspect of the present disclosure, a system is provided for accessing and monitoring a fluid within a pressurized pipe. The system includes a nozzle coupled to a section of the pressurized pipe and defining an open proximal end fluidly communicating with the pressurized pipe through an access hole formed in the pressurized pipe, an open distal end, and an interior passage extending from the open proximal end to the open distal end. A cover plate is coupled to the open distal end of the nozzle. A valve element is disposed in the interior passage and movable between an open position, in which the valve element is entirely disposed within the nozzle, and a closed position, in which a proximal section of the valve element is disposed in the pressurized pipe. A sensor port extends through a proximal end of the nozzle and positioned to fluidly communicate with the interior passage when the valve element is in the open position.

In accordance with another aspect of the present disclosure, a kit is provided for accessing and monitoring a fluid within a pressurized pipe. The kit includes a hot-tapping assembly configured to form an access hole in the pressurized pipe. The hot-tapping assembly has a nozzle coupled to a section of the pressurized pipe, the nozzle defining an open proximal end fluidly communicating with the pressurized pipe through an access hole formed in the pressurized pipe, an open distal end, and an interior passage extending from the open proximal end to the open distal end, and a cover plate coupled to the open distal end of the nozzle. The kit further includes a valve element disposed in the interior passage and movable between an open position, in which the valve element is entirely disposed within the nozzle, and a closed position, in which a proximal section of the valve element is disposed in the pressurized pipe. The kit also includes a sensor port extending through a proximal end of the nozzle and positioned to fluidly communicate with the interior passage when the valve element is in the open position.

In accordance with a further aspect of the present disclosure, a method of accessing and monitoring a fluid within a pressurized pipe includes attaching a nozzle to a section of the pressurized pipe, the nozzle defining an open proximal end, an open distal end, and an interior passage extending from the open proximal end to the open distal end. The method also includes forming an access hole in the section of the pressurized pipe so that the open proximal end of the nozzle fluidly communicates with the pressurized pipe, and inserting a valve element into the interior passage of the nozzle, the valve element being movable between an open position, in which the valve element is entirely disposed within the nozzle, and a closed position, in which a proximal section of the valve element is disposed in the pressurized pipe. The method further includes forming a sensor port through a proximal end of the nozzle that is positioned to fluidly communicate with the interior passage when the valve element is in the open position.

The features, functions, and advantages that have been discussed can be achieved independently in various embodiments or may be combined in yet other embodiments further details of which can be seen with reference to the following description and drawings.

It should be understood that the drawings are not necessarily drawn to scale and that the disclosed embodiments are sometimes illustrated schematically. It is to be further appreciated that the following detailed description is merely exemplary in nature and is not intended to limit the invention or the application and uses thereof. Hence, although the present disclosure is, for convenience of explanation, depicted and described as certain illustrative embodiments, it will be appreciated that it can be implemented in various other types of embodiments and in various other systems and environments.

DETAILED DESCRIPTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Figure 1:
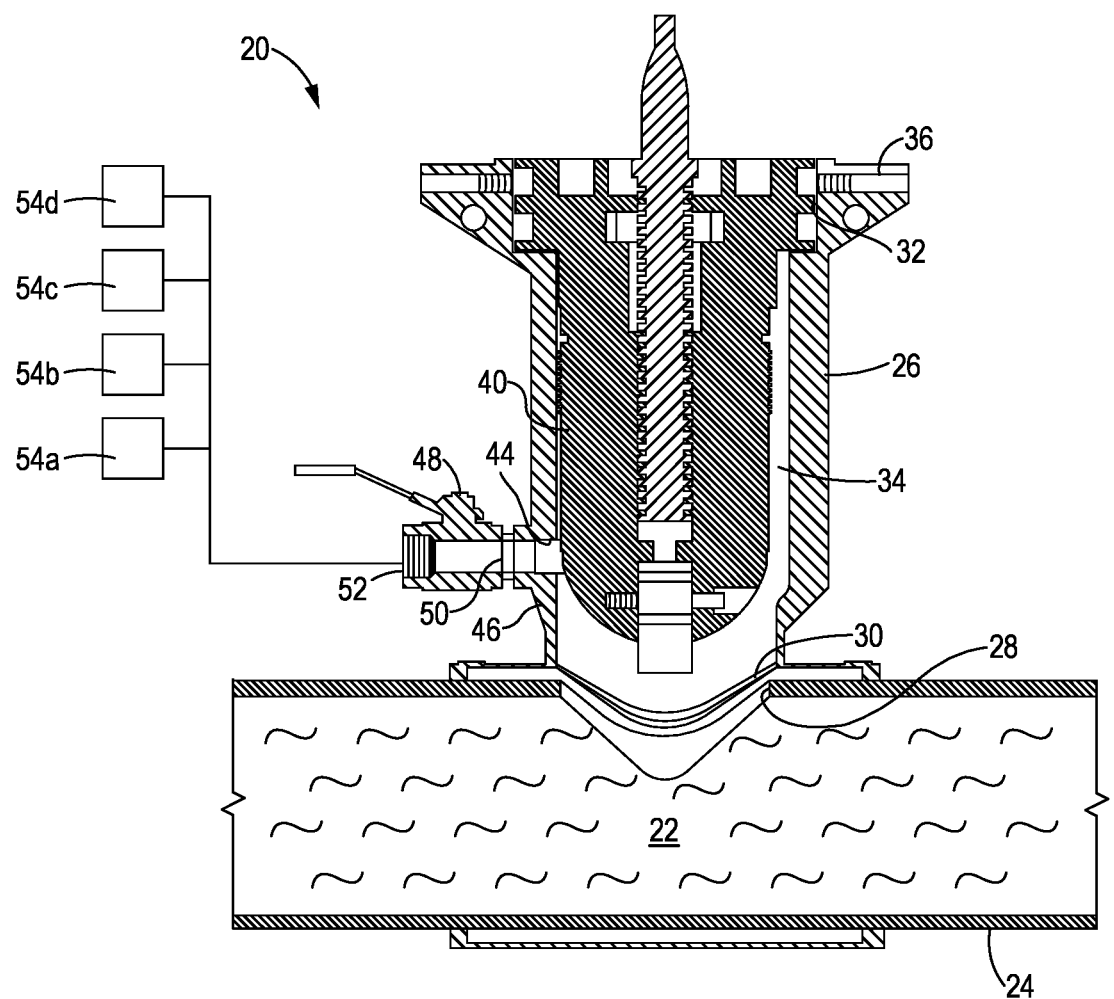
FIG. 1 is a side elevation view, in cross-section, of a system for accessing and monitoring a fluid within a pressurized pipe, according to one example of this disclosure.

One example of a system 20 for accessing and monitoring a fluid 22 within a pressurized pipe 24 is illustrated in FIG. 1. The system 20 includes a nozzle 26 coupled to a section of the pressurized pipe 24. The nozzle 26 may be attached to the pipe 24 during a hot-tapping procedure, such as disclosed in the above-noted '843 and '779 patents, the subject matter of which is expressly incorporated by reference herein. During the hot-tapping procedure, an access hole 28 is formed in the section of pressurized pipe 24. The nozzle 26 defines an open proximal end 30 fluidly communicating with the pressurized pipe 24 through the access hole 28, an open distal end 32, and an interior passage 34 extending from the open proximal end 30 to the open distal end 32. A cover plate 36 is coupled to the open distal end 32 of the nozzle 26.

Figure 6:
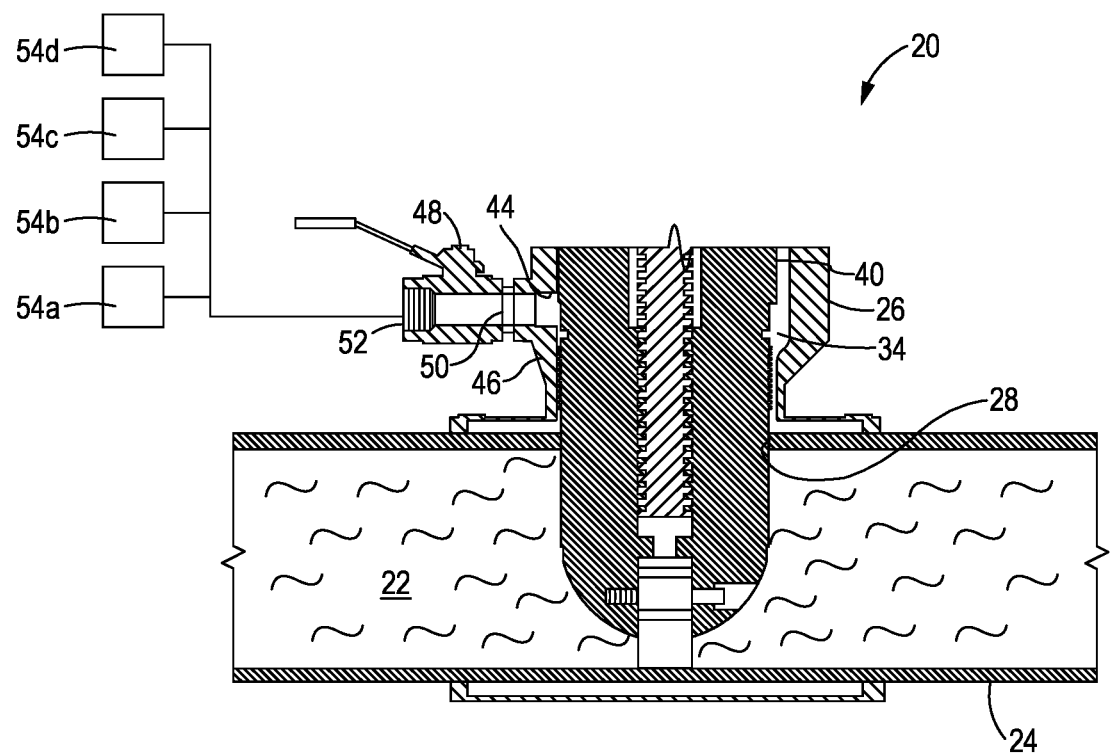
FIG. 6 is a side elevation view, in cross-section, of a system for accessing and monitoring a fluid within a pressurized pipe, with a valve element in a closed position.

The system 20 further includes a valve element 40 configured to selectively control fluid flow through the pressurized pipe 24. For example, the valve element 40 is disposed in the interior passage 34 of the nozzle 26 and is movable between an open position as shown in FIG. 1, in which the valve element 40 is entirely disposed within the nozzle 26, and a closed position, in which a proximal section 42 of the valve element 40 is disposed in the pressurized pipe 24 to sealingly engage the pipe 24 and cut off fluid flow, as shown in FIG. 6. In the example illustrated in FIG. 1, the valve element 40 is a cartridge of an insertion valve, however the valve element may be provided in other forms such as a linestop completion plug.

The system 20 also includes a sensor port 44 to provide a controlled access path into the pressurized pipe 24 for sensing one or more characteristics of the fluid 22 and/or pipe 24. As shown in FIG. 1, the sensor port 44 extends through a proximal end 46 of the nozzle 26 and is positioned to fluidly communicate with the interior passage 34 when the valve element 40 is in the open position (i.e., the sensor port 44 is not blocked off by the valve element 40 when the valve element is in the open position). A sensor valve 48 may be coupled to the sensor port 44 to provide selective access to the pressurized pipe 24. For example, the sensor valve may have a proximal end 50 fluidly communicating with the sensor port 44 and a distal end 52. The sensor valve 48 is operable to selectively control fluid communication between the sensor valve proximal end 50 and the sensor valve distal end 52.

One or more sensors 54a-d may be placed in fluid communication with the distal end 52 of the sensor valve 48. The sensors 54a-d may be configured to detect or measure various characteristics of the fluid 22 and/or pipe 24, such as fluid pressure, fluid temperature, pipe acoustics, and fluid chemistry. When the sensor valve 48 is opened, the one or more sensors 54a-d are placed in fluid communication with the fluid 22, thereby permitting detection or measurement of the desired characteristic.

Figure 2:
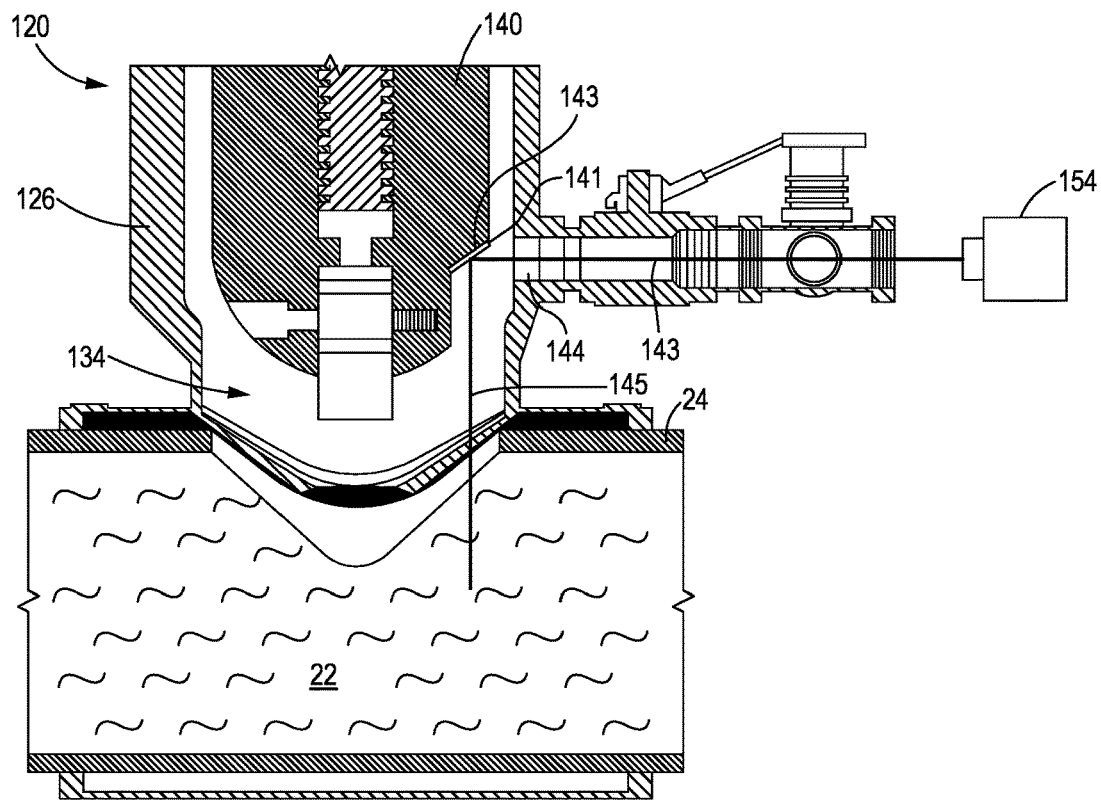
FIG. 2 is a side elevation view, in cross-section, of an alternative example of a system for accessing and monitoring a fluid within a pressurized pipe.
Figure 3:
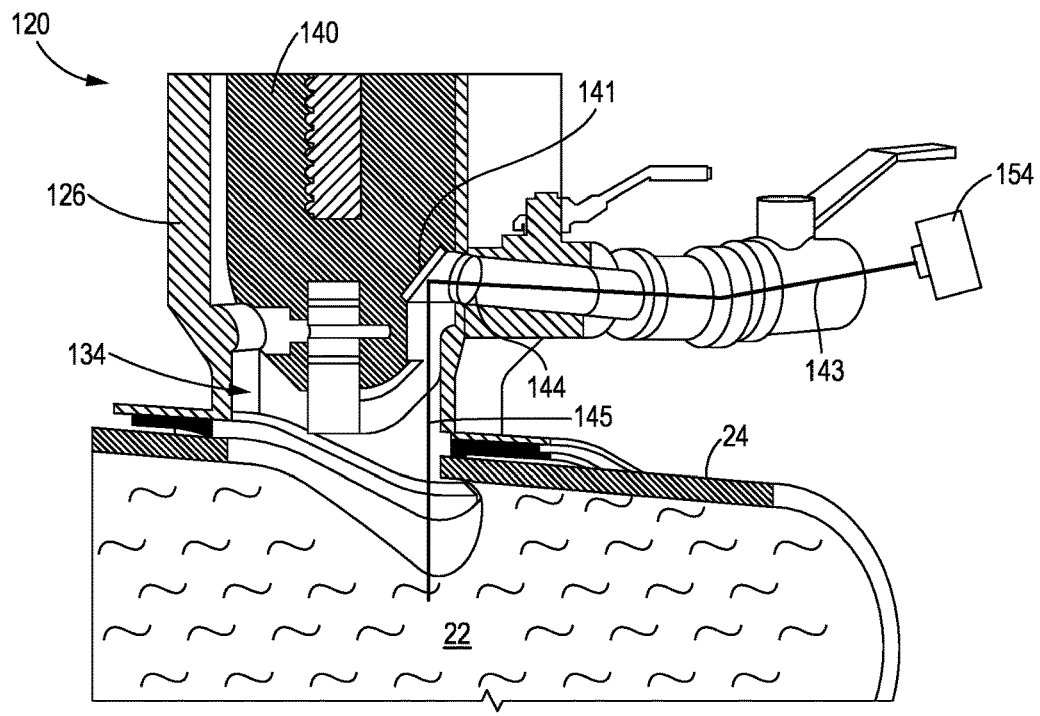
FIG. 3 is a perspective view, in cross-section, of the system of FIG. 2.

In an alternative example illustrated in FIGS. 2 and 3, a system 120 for accessing and monitoring the fluid 22 within the pressurized pipe 24 includes a valve element 140 in the form of an insertion valve. In this example, an optic reflector 141 is provided on the valve element 140 to provide a direct line of sight into the pressurized pipe 24. The optic reflector 141 is positioned in alignment with a sensor port 144 when the valve element 140 is in the open position. The optic reflector 141 is oriented to receive an incident sensor beam 143 passing through the sensor port 144 and into an interior passage 134 of a nozzle 126 that houses the valve element 140. The orientation of the optic reflector 141 further generates a reflected sensor beam 145 into the pressurized pipeline 24. The incident sensor beam 143 may be provided by a sensor 154 that requires a direct line of sight into the pressurized pipe 24, such as flow sensor. The optic reflector 141 may be a reflective surface formed directly on a portion of an exterior of the valve element 140, or may be provided as a separate component, such as a mirror, attached to the valve element 140. To accommodate the optic reflector and position it at the desired orientation, a shoulder 143 may be formed in the valve element 140.

Figure 4:
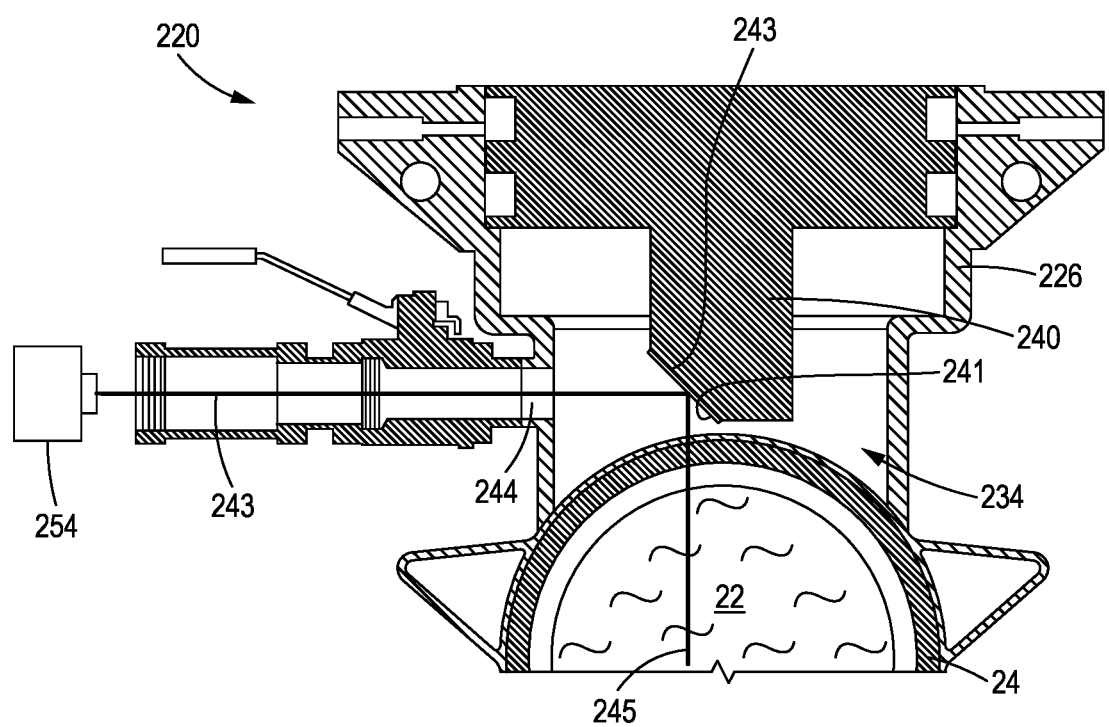
FIG. 4 is a side elevation view, in cross-section, of further alternative example of a system for accessing and monitoring a fluid within a pressurized pipe.
Figure 5:
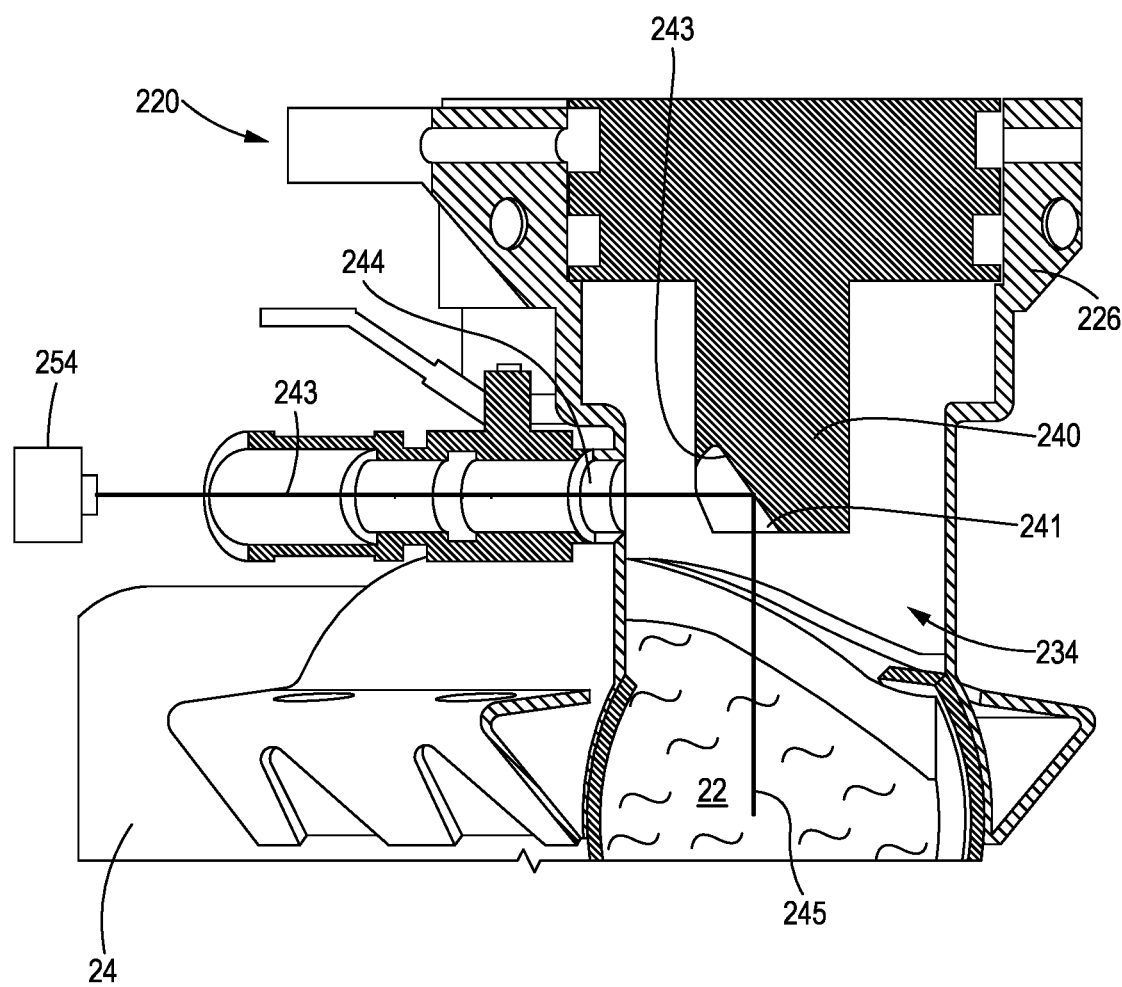
FIG. 5 is a perspective view, in cross-section, of the system of FIG. 4.

In a further alternative example illustrated in FIGS. 4 and 5, a system 220 for accessing and monitoring the fluid 22 within the pressurized pipe 24 includes a valve element 240 in the form of a linestop completion plug. In this example, an optic reflector 241 is provided on the valve element 240 to provide a direct line of sight into the pressurized pipe 24. The optic reflector 241 is positioned in alignment with a sensor port 244 when the valve element 240 is in the open position. The optic reflector surface 241 is oriented to receive an incident sensor beam 243 passing through the sensor port 244 and into an interior passage 234 of a nozzle 226 that houses the valve element 240. The orientation of the optic reflector 241 further generates a reflected sensor beam 245 into the pressurized pipeline 24. The incident sensor beam 243 may be provided by a sensor 254 that requires a direct line of sight into the pressurized pipe 24, such as flow sensor. The optic reflector 241 may be a reflective surface formed directly on a portion of an exterior of the valve element 240, or may be provided as a separate component, such as a mirror, attached to the valve element 240. To accommodate the optic reflector 241 and position it at the desired orientation, a shoulder 243 may be formed in the valve element 240.

Additionally, a kit for accessing and monitoring the fluid 22 within the pressurized pipe 24 may be provided. The kit may include any of the systems 20, 120, or 220 described above, in combination with a hot-tapping assembly configured to form the access hole 28 in the pressurized pipe 24. The hot-tapping assembly includes a nozzle 26, 126, or 226 coupled to a section of the pressurized pipe 24, and a valve element 40, 140, or 240 disposed in the interior passage. A sensor port 44, 144, or 244 extends through a proximal end of the nozzle 26, 126, or 226 and is positioned to fluidly communicate with an interior passage 34, 134, or 234 when the valve element 40, 140, or 240 is in the open position.

Still further, a method of accessing and monitoring the fluid 22 within the pressurized pipe 24 may be provided. The method includes attaching a nozzle to a section of the pressurized pipe, the nozzle defining an open proximal end, an open distal end, and an interior passage extending from the open proximal end to the open distal end. An access hole is formed in the section of the pressurized pipe so that the open proximal end of the nozzle fluidly communicates with the pressurized pipe. A valve element is inserted into the interior passage of the nozzle, the valve element being movable between an open position, in which the valve element is entirely disposed within the nozzle, and a closed position, in which a proximal section of the valve element is disposed in the pressurized pipe. The method further includes forming a sensor port through a proximal end of the nozzle positioned to fluidly communicate with the interior passage when the valve element is in the open position.

All references, including publications, patent applications, and patents, cited herein are hereby incorporated by reference. All methods described herein can be performed in any suitable order unless otherwise indicated herein or otherwise clearly contradicted by context. The use of any and all examples, or exemplary language (e.g., "such as") provided herein, is intended to illuminate the disclosed subject matter and does not pose a limitation on the scope of the claims. Any statement herein as to the nature or benefits of the exemplary embodiments is not intended to be limiting, and the appended claims should not be deemed to be limited by such statements. More generally, no language in the specification should be construed as indicating any non-claimed element as being essential to the practice of the claimed subject matter. The scope of the claims includes all modifications and equivalents of the subject matter recited therein as permitted by applicable law. Moreover, any combination of the above-described elements in all possible variations thereof is encompassed by the claims unless otherwise indicated herein or otherwise clearly contradicted by context. Additionally, aspects of the different embodiments can be combined with or substituted for one another. Finally, the description herein of any reference or patent, even if identified as "prior," is not intended to constitute a concession that such reference or patent is available as prior art against the present disclosure.

What is claimed is:

1. A system for accessing and monitoring a fluid within a pressurized pipe, the system comprising:
    a nozzle coupled to a section of the pressurized pipe, the nozzle defining an open proximal end fluidly communicating with the pressurized pipe through an access hole formed in the pressurized pipe, an open distal end, and an interior passage extending from the open proximal end to the open distal end;
    a cover plate coupled to the open distal end of the nozzle;
    a valve element disposed in the interior passage and movable between an open position, in which the valve element is entirely disposed within the nozzle and entirely outside of the pressurized pipe, and a closed position, in which a proximal section of the valve element is disposed in the pressurized pipe and sealingly engages the pressurized pipe to cut off fluid flow through the pressurized pipe; and
    a sensor port extending through a proximal end of the nozzle and positioned to fluidly communicate with the interior passage when the valve element is in the open position.

2. The system of claim 1, further comprising a sensor in fluid communication with the sensor port.

3. The system of claim 2, further comprising a sensor valve having a proximal end, fluidly communicating with the sensor port, and a distal end, fluidly communicating with the sensor, the sensor valve being operable to selectively control fluid communication between the sensor valve proximal end and the sensor valve distal end.

4. The system of claim 1, further comprising a plurality of sensors in fluid communication with the sensor port.

5. The system of claim 1, in which the valve element includes an optic reflector positioned to align with the sensor port when the valve element is in the open position, the optic reflector being oriented to receive an incident sensor beam passing through the sensor port and into the interior passage and generate a reflected sensor beam into the pressurized pipe.

6. The system of claim 5, in which the valve element comprises a cartridge of an insertion valve.

7. The system of claim 5, in which the valve element comprises a linestop completion plug.

8. A kit for accessing and monitoring a fluid within a pressurized pipe, the kit comprising:
    a hot-tapping assembly configured to form an access hole in the pressurized pipe, the hot-tapping assembly including:
    a nozzle coupled to a section of the pressurized pipe, the nozzle defining an open proximal end fluidly communicating with the pressurized pipe through an access hole formed in the pressurized pipe, an open distal end, and an interior passage extending from the open proximal end to the open distal end; and
    a cover plate coupled to the open distal end of the nozzle;
    a valve element disposed in the interior passage and movable between an open position, in which the valve element is entirely disposed within the nozzle and entirely outside of the pressurized pipe, and a closed position, in which a proximal section of the valve element is disposed in the pressurized pipe and sealingly engages the pressurized pipe to cut off fluid flow through the pressurized pipe; and
    a sensor port extending through a proximal end of the nozzle and positioned to fluidly communicate with the interior passage when the valve element is in the open position.

9. The kit of claim 8, further comprising a sensor in fluid communication with the sensor port.

10. The kit of claim 9, further comprising a sensor valve having a proximal end, fluidly communicating with the sensor port, and a distal end, fluidly communicating with the sensor, the sensor valve being operable to selectively control fluid communication between the sensor valve proximal end and the sensor valve distal end.

11. The kit of claim 8, further comprising a plurality of sensors in fluid communication with the sensor port.

12. The kit of claim 8, in which the valve element includes an optic reflector positioned to align with the sensor port when the valve element is in the open position, the optic reflector being oriented to receive an incident sensor beam passing through the sensor port and into the interior passage and generate a reflected sensor beam into the pressurized pipe.

13. The kit of claim 12, in which the valve element comprises a cartridge of an insertion valve.

14. The kit of claim 12, in which the valve element comprises a linestop completion plug.

15. A method of accessing and monitoring a fluid within a pressurized pipe, the method comprising:
    attaching a nozzle to a section of the pressurized pipe, the nozzle defining an open proximal end, an open distal end, and an interior passage extending from the open proximal end to the open distal end;
    forming an access hole in the section of the pressurized pipe so that the open proximal end of the nozzle fluidly communicates with the pressurized pipe;
    inserting a valve element into the interior passage of the nozzle, the valve element being movable between an open position, in which the valve element is entirely disposed within the nozzle and entirely outside of the pressurized pipe, and a closed position, in which a proximal section of the valve element is disposed in the pressurized pipe and sealingly engages the pressurized pipe to cut off fluid flow through the pressurized pipe; and
    forming a sensor port through a proximal end of the nozzle positioned to fluidly communicate with the interior passage when the valve element is in the open position.

16. The method of claim 15, further comprising sensing a characteristic of the fluid and/or the pressurized pipe via the sensor port using a sensors.

17. The method of claim 15, further comprising sensing a plurality of characteristics of the fluid and/or the pressurized pipe via the sensor port using a plurality of sensors.

18. The method of claim 15, further comprising providing a direct line of sight through the sensor port to the pressurized pipe by providing an optic reflector on the valve element that is positioned to align with the sensor port when the valve element is in the open position, the optic reflector being oriented to receive an incident sensor beam passing through the sensor port and into the interior passage and generate a reflected sensor beam into the pressurized pipe.

19. The method of claim 18, in which the valve element comprises a cartridge of an insertion valve.

20. The method of claim 18, in which the valve element comprises a linestop completion plug.

\* \* \* \* \*